United States Patent [19]

Chaumette et al.

[11] Patent Number: 5,723,505
[45] Date of Patent: Mar. 3, 1998

[54] PROCESS FOR THE CONVERSION OF NATURAL GAS TO HYDROCARBONS

[75] Inventors: Patrick Chaumette, Bougival; Pierre Boucot, Ternay, both of France

[73] Assignee: Institut Francais du Petrole, Rueil Malmaison, France

[21] Appl. No.: 428,550

[22] Filed: Apr. 25, 1995

[30] Foreign Application Priority Data

Apr. 25, 1994 [FR] France .................. 94 05065

[51] Int. Cl.$^6$ .................................. C07C 27/00
[52] U.S. Cl. .................. 518/702; 518/703
[58] Field of Search .............. 518/700, 702, 518/703; 585/785

[56] References Cited

U.S. PATENT DOCUMENTS 5,023,276  6/1991  Yarrington et al. .......... 514/703

FOREIGN PATENT DOCUMENTS 0 142 888  5/1985  European Pat. Off. .

*Primary Examiner*—Jose' G. Dees
*Assistant Examiner*—Karl J. Puttlitz, Jr.
*Attorney, Agent, or Firm*—Millen, White, Zelano, & Branigan, P.C.

[57] ABSTRACT

A process for the preparation of essentially linear and saturated hydrocarbons from natural gas (1), comprising the following successive steps, the order of steps (b) and (c) being exchangeable or said steps being capable of being conducted simultaneously:

(a) producing (6) synthesis gas (7) by treatment of said gas.

(b) mixing an effluent comprising at least the synthesis gas (7) obtained from the preceding step and an effluent (4) comprising mainly $C_2$–$C_4$ hydrocarbons, (c) cooling an effluent comprising at least the mixture obtained from the preceding step, (d) transforming the effluent (8) obtained from step (c) in a cracking zone (10), (e) separating (12) the effluent obtained at step (d) into an effluent comprising mainly water (13) and an anhydrous effluent (14), and (f) transforming (15) the effluent obtained from step (e) (14) by a Fischer-Tropsch synthesis.

11 Claims, 1 Drawing Sheet

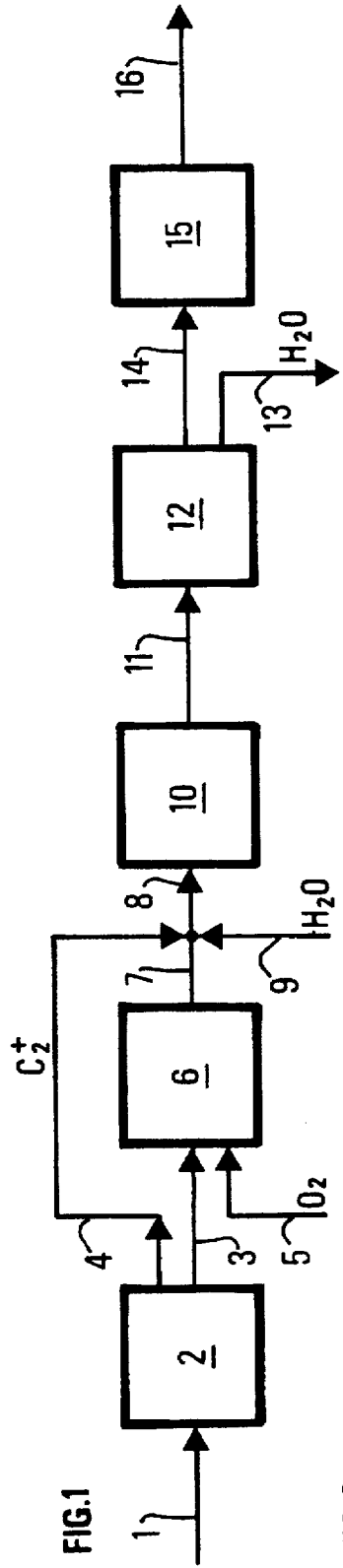
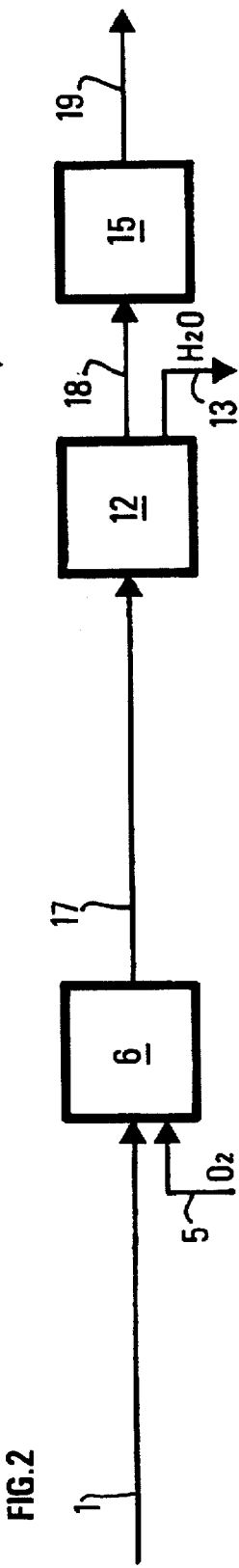
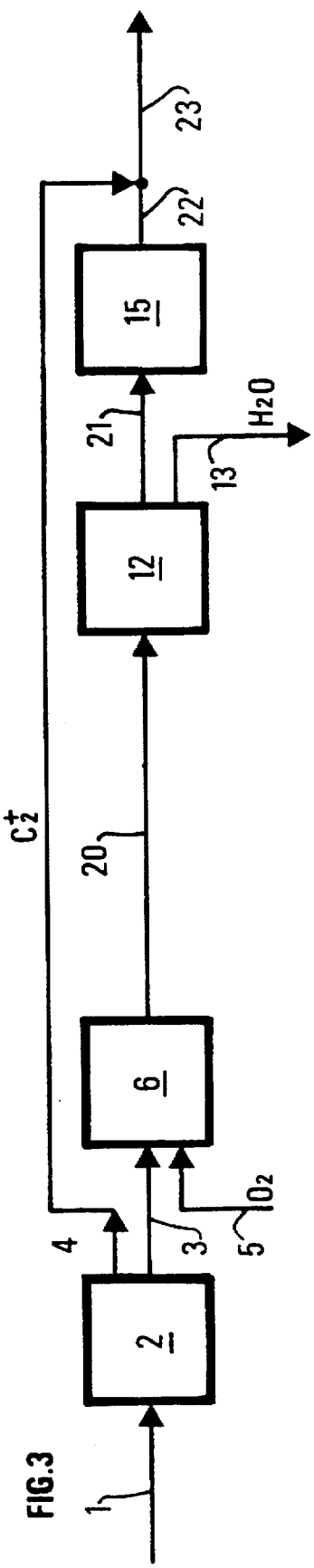

PROCESS FOR THE CONVERSION OF NATURAL GAS TO HYDROCARBONS

BACKGROUND OF THE INVENTION

The present invention concerns a process for the production of essentially linear and saturated hydrocarbons, preferably comprising a large proportion of hydrocarbons containing at least 5 carbon atoms per molecule ($C_5^+$), from a natural gas.

Natural gas is an abundant fossil material which is mainly constituted by methane but which often contains large quantities of ethane and $C_3^+$ hydrocarbons (hydrocarbons containing at least 3 carbon atoms per molecule), mainly $C_2$–$C_4$ (hydrocarbons containing 2 to 4 carbon atoms per molecule), as well as other constituents such as water ($H_2O$), carbon dioxide ($CO_2$), nitrogen ($N_2$), hydrogen sulphide ($H_2S$) and helium (He).

Natural gas is generally purified; purification consists of, among others, removing at least the hydrogen sulphide, water and helium.

After purification, the natural gas, with a sulphide compound content of preferably less than 10 ppm, contains mainly methane (for example, 55–99% by volume), but also $C_2^+$ hydrocarbons, mainly $C_2$–$C_4$, and may also contain small quantities of nitrogen and/or carbon dioxide.

Due to the use of loose language, the term natural gas is conventionally used to refer both to the gas from a field without any prior purification and to the purified gas obtained after dehydration and desulphuration.

The skilled person is aware that natural gas can be transformed into synthesis gas (i.e., a mixture containing carbon monoxide, hydrogen and perhaps carbon dioxide, said mixture being abbreviated below as CO—($CO_2$)—$H_2$). This transformation can be carried out using a number of procedures such as water reforming, currently carried out in two reaction steps, or partial oxidation (Ulmann's Encyclopedia of Industrial Chemistry Volume A12, p 186–212).

In order to improve the thermal yield (i.e., the ratio between the heating value of the gas obtained after reforming or partial oxidation and that of the natural gas feed), an autothermal reforming process has been proposed which is operated in the presence of water and air (Ulmann's Encyclopedia of Industrial Chemistry Volume A12, p 202; French patent application FR-A-2 679 217).

The skilled person is also aware that synthesis gas can be converted into hydrocarbons in the presence of a catalyst containing at least one transition metal. This reaction is known in the literature as the Fischer-Tropsch synthesis (Ulmann's Encyclopedia of Industrial Chemistry Volume A7, p 206). The catalyst which is normally used for this synthesis generally contains at least one metal from groups 6 to 11 such as iron, ruthenium, cobalt or nickel (Catalysis Letters vol 7, p 303, 1990). The products prepared by the Fischer-Tropsch synthesis in the presence of this metallic catalyst have a very wide distribution of molecular weights. A large proportion of the hydrocarbons produced contain more than carbon atoms per molecule ($C_5^+$ hydrocarbons); in addition, these hydrocarbon products are mainly essentially linear and saturated hydrocarbons with high boiling points, i.e., with boiling points which are above the middle distillate range (the kerosine fraction in which the boiling points are respectively between 140° C. and 300° C. and the gas oil fraction with boiling points of between 180° C. and 370° C. It is often advantageous to treat at least a portion of the hydrocarbons produced during the Fischer-Tropsch synthesis in a catalytic hydrotreatment process operated in the presence of hydrogen. The catalyst used in this process preferably contains at least one metal from groups 6 to 11, which metal has a hydrogenating activity, said metal being dispersed on a support. This process primarily transforms high boiling point hydrocarbons into lighter products and thus significantly increases the middle distillate yield.

However, the combination of processes comprising transformation of natural gas into synthesis gas, the Fischer-Tropsch synthesis and the optional hydrotreatment process also produces light, saturated and unsaturated hydrocarbons containing at most 4 carbon atoms per molecule ($C_4^-$ hydrocarbons), mainly $C_2$–$C_4$, which are hard to valorise i.e., to increase in value. United States patent U.S. Pat. No. 4,587,008 describes recycling at least a portion of the hydrocarbons to the synthesis gas production step.

SUMMARY OF THE INVENTION

The process of the present invention converts natural gas into essentially linear and saturated hydrocarbons, preferably containing a high proportion of $C_5^+$ hydrocarbons, and also advantageously valorises the essentially linear and saturated $C_2^+$ hydrocarbons, mainly $C_2$–$C_4$, contained in the natural gas. It can also convert at least a portion of the essentially linear and saturated $C_4^-$ hydrocarbons, mainly $C_2$–$C_4$, from the Fischer-Tropsch synthesis and the optional hydrotreatment process.

The process of the present invention is a process for the preparation of essentially linear and saturated hydrocarbons which preferably contain a high proportion of $C_5^+$ hydrocarbons from a feed containing essentially natural gas, said process comprising the following successive steps, steps (b) and (c) being capable of being carried out either simultaneously or in the order (b) then (c) or in the order (c) then (b):

(a) producing synthesis gas by treating at least a portion of said feed to obtain an effluent containing mainly carbon monoxide, hydrogen and optionally carbon dioxide, (b) mixing an effluent comprising at least a major portion of the effluent obtained from the preceding step with an effluent comprising mainly at least one hydrocarbon containing 2 to 4 carbon atoms per molecule, (c) cooling an effluent comprising at least the major portion of the mixture obtained from the preceding step, to produce a cooled effluent, (d) transforming the major portion of the cooled effluent from the preceding step in a cracking zone, to obtain an effluent comprising unsaturated hydrocarbons, (e) separating at least a major portion of the effluent from step (d) into an effluent comprising mainly water and an effluent which is practically free of water, (f) transforming at least a major portion of the practically water-free effluent from step (e) by a Fischer-Tropsch synthesis, in the presence of a Fischer-Tropsch synthesis catalyst to produce the final effluent.

When steps (b) and (c) are carried out simultaneously, a step is carried out following step (a), in which at least a major portion of the effluent from step (a) is mixed with an effluent comprising mainly at least one $C_2$–$C_4$ hydrocarbon and cooled, to produce a cooled effluent.

When steps (b) and (c) are carried out in the order (b) then (c), the following steps are carried out following step (a) and before step (d):

(b) mixing an effluent comprising at least a major portion of the effluent obtained from step (a) with an effluent comprising mainly at least one $C_2$–$C_4$ hydrocarbon, (c) cooling an effluent comprising at least the major portion of the mixture obtained from step (b), to produce a cooled effluent. When steps (b) and (c) are carried out in the order (c) then (b), the following steps are carried out following step (a) and before step (d):

(c) cooling an effluent comprising at least the major portion of the mixture obtained from step (a), to produce a cooled effluent, (b) mixing an effluent comprising at least a major portion of the effluent obtained from step (b) with an effluent comprising mainly at least one $C_2$–$C_4$ hydrocarbon, which may be cooled.

In a preferred embodiment of the process of the invention, the effluent comprising mainly at least one hydrocarbon containing 2 to 4 carbon atoms per molecule is preferably at least partially produced by at least one of the following processes: a Fischer-Tropsch synthesis process, or a hydrotreatment process; in the preferred case, said effluent can, of course, be an effluent from the process of the invention.

In a preferred embodiment of the process of the invention, the effluent from step (f) is separated into a first effluent containing mainly essentially linear and saturated hydrocarbons containing 2 to 4 carbon atoms per molecule and a second effluent containing mainly essentially linear and saturated hydrocarbons containing at least five carbon atoms per molecule. In this preferred embodiment, the effluent comprising mainly at least one $C_2$–$C_4$ hydrocarbon from step (b) comprises at least a major portion of said first effluent obtained from step (f). However, in the case of this preferred embodiment, hydrotreatment is preferably carried out on said second effluent after step (f). More preferably still, the effluent comprising mainly at least one $C_2$–$C_4$ hydrocarbon from step (b) comprises at least a major portion of an effluent comprising mainly $C_2$–$C_4$ hydrocarbons from the hydrotreatment step.

The process of the invention is preferably carried out such that, prior to step (a) of the process of the invention, the feed is separated into a first methane-enriched fraction, i.e., containing at least 85 molar % of methane, preferably at least 90 molar % of methane and more preferably at least 95 molar % of methane, and into a second fraction which is enriched in at least one $C_2^+$ hydrocarbon, mainly $C_2$–$C_4$, i.e., comprising at least 85 molar % of $C_2^+$, mainly $C_2$–$C_4$, preferably at least 90 molar % of $C_2^+$ hydrocarbon and more preferably at least 95molar % of $C_2^+$ hydrocarbon, mainly $C_2$–$C_4$, such that the portion of said feed treated at step (a) is mainly the major portion of said first fraction. In the case of this preferred process of the invention, the effluent containing mainly at least one $C_2$–$C_4$ hydrocarbon from step (b) comprises at least a major portion of said second fraction (generally containing a high proportion of ethane).

Step (d) involving cracking of the mainly $C_2$–$C_4$ hydrocarbons transforms these hydrocarbons, which are essentially linear and saturated and inert in the Fischer-Tropsch synthesis reaction, into essentially unsaturated hydrocarbons which constitute chain initiators in that reaction (A A ADESINA, R R HUDGINS and P L SILVESTON, Applied Catalysis vol 61, p 295, 1990; P CHAUMETTE, C VERDON, A KIENNEMANN, S BOUJANA, A C S Div. Pet. Chem, Vol 37, no 3, p 833, Apr. 1992). For the Fischer-Tropsch synthesis, this results in an improvement in the selectivity towards $C_5^+$ hydrocarbons and better valorisation of light $C_1$–$C_4$ hydrocarbons.

The different steps which can be included in the embodiment of the process of the invention described above are steps which are known to the skilled person. Nevertheless, some details will be given below.

Step (a) for the production of the synthesis gas is preferably a partial oxidation step for at least a portion of the feed comprising essentially natural gas (fuel) in the presence of an oxidant in a combustion chamber and optionally comprising at least one injection means for a complementary fuel, steam which may be added with the oxidant or the fuel in the combustion chamber. The methane-enriched combustible feed can optionally be mixed with a CO—($CO_2$)—$H_2$ effluent. The oxidant used in this step can be pure oxygen, or oxygen mixed with an inert gas such as nitrogen, steam or carbon dioxide.

A reaction zone termed an autothermal reforming zone can also be employed for step (a), comprising a non catalytic combustion chamber and at least one catalytic bed into which the gases from the combustion chamber flow; the combustion chamber used must thus be able to operate with a short residence time and with a lack of oxygen, as described in French patent application FR-A-2 79 217.

Step (a) of the process of the invention is thus preferably operated without a catalyst (for partial oxidation) and at a temperature which is generally between 1000° and 1500°, preferably between 1200° C. and 400° C.

When step (a) of the process of the invention is operated in the presence of a catalyst, a corrected hourly space velocity (VVH) is used which is between 200 and 10000 h$^{-1}$, preferably between 400 and 8000 h$^{-1}$, where the corrected VVH is equal to m×VVH, if m is the average number of carbon atoms of the feed, Preferably, the following molar ratio is used:

$$\frac{[H_2O + CO_2]}{\Sigma C} < 1.5$$

where $\Sigma C$ represents all the carbon in the hydrocarbons, and where ($H_2O+CO_2$) represents the sum of the flow rates of the injected water and $CO_2$.

Preheating is advisable, both for the fuel and for the oxidant, before introduction into the reactor. Preferably, the fuel is preheated to between 100° C. and 850° C., while the oxidising agent can be preheated to between 100° C. and 900° C., preferably between 200° C. and 750° C.

The pressure in the combustion chamber is generally between 0.1 and 15 MPa, preferably between 2 and 10 MPa (1 MPa=$10^6$ Pa).

The cooling step is preferably carried out by addition of water (quench). In this case, the water added, in weight % with respect to the effluent to be cooled, is between 0.1 and 80, preferably between 1 and 15.

The transformation step in the cracking zone for the major portion of the cooled effluent from the preceding step (step (d) of the invention) does not in general require the use of a catalyst. It is carried out at a temperature of between 700° C. and 1300° C., preferably between 800° C. and 1100° C. The pressure has no absolute value as the pressure drop in the cracking reactor can be as high as several bars (1 bar=105 Pa).

Since increasing the pressure inhibits the cracking reactions, it is usual to operate at the lowest pressure which is compatible with the pressure drops and with the pressure used in the following step, i.e., between 0.1 and 6 MPa, preferably between 1 and 4 MPa, for example.

Transformation of at least a major portion of the practically water-free effluent from step (e) by the Fischer-Tropsch synthesis (step (f) of the invention) is generally carried out at a total pressure which is normally between 0.1 and 15 MPa, preferably between 0.5 and 10 MPa, the temperature being generally between 150° C. and 350° C., preferably between 170° C. and 300° C.

The hourly space velocity is normally between 100 and 10000 volumes of effluent per volume of catalyst per hour, preferably between 400 and 5000 volumes of effluent per volume of catalyst per hour, and the $H_2/CO$ ratio in the synthesis gas is normally between 1:1 and 3:1, preferably between 1.2:1 and 2.5:1.

The catalyst for step (f) can be used as a fine grade powder [normally 10–700 μm (1 μm=$10^{-6}$m)]or as particles with an equivalent diameter of generally between 2 and 10 mm, in the presence of a gaseous phase, or in the presence of a liquid and a gaseous phase under operating conditions. The liquid phase can be constituted by at least one hydrocarbon containing at least 5 and preferably at least 10 carbon atoms per molecule. The catalyst is generally based on at least one metal from groups 6 to 11, and preferably contains at least cobalt or iron, dispersed on a support based on at least one metallic oxide, preferably silica, alumina or titanium oxide. Preferably, a cobalt based catalyst such as that described in European patent application EP-A-0 581 619, is used. Any known catalyst may, however, be used.

BRIEF DESCRIPTION OF THE DRAWINGS

The attached FIGS. 1,2 and 3 are a block flowsheet of a comprehensive embodiment of the invention.

The following non limiting Example 1 represents an embodiment of the process of the invention which can be used to convert a feed containing essentially natural gas into essentially linear and saturated hydrocarbons, and advantageously valorise the essentially linear and saturated $C_2^+$ contained in that feed. The Example is illustrated by the accompanying Figures.

EXAMPLE 1

(in accordance with the invention)

Natural gas (1) containing 92% of methane and 8% of ethane (percentages expressed as % of carbon, i.e., in moles of carbon per mole of carbon contained in the natural gas introduced) was introduced into a separating unit (2). A first fraction (3) containing essentially methane and a second fraction (4) containing the $C_2^+$ hydrocarbons (essentially ethane) were obtained from the outlet to this unit. The compositions of the effluents are given in Table 1 and the flowsheet of the process is shown in the FIG. 1.

The methane-rich fraction (3) was introduced into a partial oxidation reactor (6) where it was converted into synthesis gas (7) using oxygen (5). The reactor was operated at a temperature of 1260° C. and a pressure of 3 MPa.

The ethane-rich fraction (4) and water (9) were added to the synthesis gas (7) to produce an effluent (8) which reduced (quenched) the temperature of the effluent from the partial oxidation unit before it entered the cracking reactor (10).

Effluent (8) was cracked at a pressure of 3 MPa, an inlet temperature of 800° C. and with a residence time of the feed in the cracking reactor of 2.4 sec. Effluent (11) at the outlet of reactor (10) was at a temperature of 730° C.

After separating out the water (13) in the separating unit (12), the essentially anhydrous effluent (14) was sent to the Fischer-Tropsch synthesis unit (15) which was also operated at 3 MPa, but at a temperature of 240° C. and a VVH of 2000 $h^{-1}$, to convert it to a mixture of hydrocarbons (effluent 16) in the presence of a catalyst comprising 20% of cobalt, 0.8% of ruthenium and 0.2% of copper on silica.

Table 1 shows that the combination of a partial oxidation step (6) and hydrocarbon cracking step (10) produced a $H_2/CO$ ratio of close to 2 at the inlet to the Fischer-Tropsch synthesis reactor, i.e., a value which is close to the stoichiometry of the hydrocarbon synthesis reactions.

The cracking step converted practically all of the ethane into ethylene (see Table 1, product 11), which contributed to the hydrocarbon synthesis in the Fischer-Tropsch reactor.

This naturally produced higher productivity and selectivity towards $C_5^+$ hydrocarbons (respectively, 0.6228 moles of $C_5^+$ hydrocarbons per mole of carbon introduced and 85.22% of $C_5^+$ hydrocarbons).

EXAMPLE 2

(comparative)

Natural gas (1) containing 92% of methane and 8% of ethane (percentages expressed as % of carbon) was introduced into partial oxidation reactor (6) where it was converted into synthesis gas (17) using oxygen (5). The reactor was operated at a temperature of 1260° C. and at a pressure of 3 MPa. The compositions of the different effluents are given in Table 2 and the diagram of the process is shown in FIG. 2. The synthesis gas produced had a $H_2/CO$ ratio of 1.21.

After separating out the water (13) in the separating unit (12), the essentially anhydrous effluent (18) was sent to the Fischer-Tropsch synthesis unit (15) which was also operated at 3 MPa, but at a temperature of 240° C. and a VVH of 2000 $h^{-1}$ to convert it to an effluent (19) (see Table 2). The low $H_2/CO$ ratio in the anhydrous synthesis gas (18) resulted in a much lower $C_5^+$ productivity than that of Example 1 of the invention (0.4428 moles per mole of carbon introduced).

EXAMPLE 3

(comparative)

Natural gas (1) containing 92% of methane and 8% of ethane (percentages expressed as % of carbon) was first separated into 2 fractions in a separating unit (2). A first fraction (3) containing essentially methane and a second fraction (4) containing the $C_2^+$ hydrocarbons (essentially ethane) were obtained at the outlet to this unit. The compositions of the effluents are given in Table 3 and the diagram of the process is shown in FIG. 3.

The methane-rich fraction (3) was introduced into partial oxidation reactor (6) where it was converted into synthesis gas (20) using oxygen (5). The reactor was operated at a temperature of 1260° C. and a pressure of 3 MPa.

the synthesis gas produced (20) had a $H_2/CO$ ratio of 1.88. Effluent (21) obtained after separation of the water in the separating unit (12) was introduced into the Fischer-Tropsch synthesis reactor (15) where it was transformed into an effluent (22) to which was added the effluent from line (4) to obtain the final effluent (23) (Table 3). The Fischer-Tropsch synthesis unit was operated at 3 MPa, 240° C., with a VVH of 2000 $h^{-1}$. The productivity and selectivity towards the $C_5^+$ hydrocarbons obtained were much lower than those of Example 1 in accordance with the invention.

TABLE 1

Compositions of effluents from Example 1 expressed as moles of carbon per mole of carbon in the natural gas introduced.

| Effluent | 1 | 3 | 4 | 7 | 8 | 11 | 14 | 16 | Selectivity (% C) |
|---|---|---|---|---|---|---|---|---|---|
| $CH_4$ | 0,92 | 0,92 | 0 | 0,0089 | 0,0089 | 0,0134 | 0,0134 | 0,0467 | 6,39 |
| $C_2H_4$ | 0 | 0 | 0 | 0 | 0 | 0,0751 | 0,0751 | | |
| $C_2H_6$ | 0,08 | 0 | 0,08 | 0 | 0,0784 | 0,0001 | 0,0001 | 0,0240 | 3,28 |
| $C_3-C_4$ | 0 | 0 | 0 | 0 | 0 | 0,0003 | 0,0003 | | |
| $C_5^+$ | 0 | 0 | 0 | 0 | 0 | 0 | 0 | 0,6228 | 85,22 |
| $H_2$ | 0 | 0 | 0 | 1,6581 | 1,6609 | 1,7321 | 1,7321 | 0,2533 | — |
| CO | 0 | 0 | 0 | 0,8822 | 0,8837 | 0,8808 | 0,8808 | 0,1938 | — |
| $CO_2$ | 0 | 0 | 0 | 0,0289 | 0,0289 | 0,0304 | 0,0304 | 0,0373 | 5,10 |
| $H_2O$ | 0 | 0 | 0 | 0,1640 | 1,4679 | 1,4595 | 0 | 0,6732 | — |
| $H_2/CO$ | — | — | — | 1,88 | 1,88 | 1,97 | 1,97 | 1,31 | — |

TABLE 2

Compositions of effluents from Example 2 expressed as moles of carbon per mole of carbon in the natural gas introduced.

| Effluent | 1 | 17 | 18 | 19 | Selectivity (% C) |
|---|---|---|---|---|---|
| $CH_4$ | 0,92 | 0 | 0 | 0,0195 | 3,58 |
| $C_2H_4$ | 0 | 0 | 0 | | |
| $C_2H_6$ | 0,08 | 0 | 0 | 0,0097 | 1,79 |
| $C_3-C_4$ | 0 | 0 | 0 | | |
| $C_5^+$ | 0 | 0 | 0 | 0,4428 | 81,54 |
| $H_2$ | 0 | 1,2262 | 1,2262 | 0,2275 | — |
| CO | 0 | 1,0138 | 1,0138 | 0,5272 | — |
| $CO_2$ | 0 | 0,0662 | 0,0662 | 0,0711 | 13,08 |
| $H_2O$ | 0 | 0,8538 | 0,8538 | 1,3210 | — |
| $H_2/CO$ | — | 1,21 | 1,21 | 0,43 | — |

TABLE 3

Compositions of effluents from Example 3 expressed as moles of carbon per mole of carbon in the natural gas introduced.

| Effluent | 1 | 3 | 4 | 20 | 21 | 22 | 23 | Selectivity (% C) |
|---|---|---|---|---|---|---|---|---|
| $CH_4$ | 0,92 | 0,92 | 0 | 0,0089 | 0,0089 | 0,0612 | 0,0612 | 7,85 |
| $C_2H_4$ | 0 | 0 | 0 | 0 | 0 | | | — |
| $C_2H_6$ | 0,08 | 0 | 0,08 | 0 | 0 | 0,0232 | 0,1032 | 13,23 |
| $C_3-C_4$ | 0 | 0 | 0 | 0 | 0 | | | — |
| $C_5^+$ | 0 | 0 | 0 | 0 | 0 | 0,5796 | 0,5796 | 74,36 |
| $H_2$ | 0 | 0 | 0 | 1,6581 | 1,6581 | 0,2338 | 0,2338 | — |
| CO | 0 | 0 | 0 | 0,8822 | 0,8822 | 0,2206 | 0,2206 | — |
| $CO_2$ | 0 | 0 | 0 | 0,0289 | 0,0289 | 0,0355 | 0,0355 | 4,55 |
| $H_2O$ | 0 | 0 | 0 | 0,1640 | 0 | 0,8125 | 0,8125 | — |
| $H_2/CO$ | — | — | — | 1,88 | 1,88 | 1,06 | 1,06 | — |

We claim:

1. A process comprising:
   cracking a cooled effluent comprising a synthesis gas containing carbon monoxide, hydrogen and, optionally, carbon dioxide, and at least one hydrocarbon of 2–4 carbon atoms per molecule in a cracking zone to obtain an effluent comprising unsaturated hydrocarbons prepared by the cracking,
   separating water from said effluent to obtain an essentially water-free effluent, and
   subjecting said essentially water-free effluent to a Fischer-Tropsch synthesis in the presence of a Fischer-Tropsch synthesis catalyst to obtain a final effluent containing essentially linear and saturated hydrocarbons including $C_5^+$ hydrocarbons.

2. The process of claim 1, wherein the synthesis gas is prepared from a feed comprising natural gas.

3. A process according to claim 1, wherein the at least one hydrocarbon containing 2 to 4 carbon atoms per molecule is provided at least partially from the effluent of the Fischer-Tropsch synthesis.

4. A process according to claim 1, wherein the final effluent is separated into a first fraction containing essentially linear and saturated hydrocarbons of 2 to 4 carbon atoms per molecule and second fraction containing essentially linear and saturated hydrocarbons of at least five carbon atoms per molecule.

5. A process according to claim 4, wherein at least a portion of said separated first fraction is recycled as at least a portion of the at least one hydrocarbon of 2–4 carbon atoms for the cracking.

6. A process according to claim 4, wherein hydrotreatment of said second fraction is carried out after its separation.

7. A process according to claim 6, wherein an effluent comprising $C_2-C_4$ hydrocarbons from the hydrotreatment step is recycled as at least a portion of the at least one hydrocarbon of 2–4 carbon atoms for the cracking.

8. A process according to claim 3 wherein, prior to preparation of the synthesis gas, the feed comprising natural gas is separated into a first methane-enriched fraction which is used to prepare the synthesis gas and into a second fraction which is enriched in at least one hydrocarbon containing 2 to 4 carbon atoms per molecule.

9. A process according to claim 8, wherein the second fraction enriched in at least one hydrocarbon containing 2 to 4 carbon atoms is used for at least a portion of the at least one hydrocarbon of 2-4 carbon atoms in the cracking.

10. A process according to claim 3 wherein the synthesis gas is produced by partial oxidation of at least a portion of the feed comprising natural gas.

11. The process of claim 1, wherein the cracking is conducted without a catalyst.

* * * * *